(12) United States Patent
Rauchschwalbe et al.

(10) Patent No.: US 8,642,816 B2
(45) Date of Patent: Feb. 4, 2014

(54) METHOD FOR ISOLATING DI-TRIMETHYLOL PROPANE

(75) Inventors: Gunter Rauchschwalbe, Leverkusen (DE); Ulrich Notheis, Dormagen (DE); Michael Friederich, Krefeld (DE); Hans-Dieter Gerriets, Duisburg (DE); Carsten Hummelt, Köln (DE); Christiane Oppenheimer-Stix, Neuss (DE); Paul Wagner, Düsseldorf (DE)

(73) Assignee: LANXESS Deutschland GmbH, Cologne (DE)

( * ) Notice: Subject to any disclaimer, the term of this patent is extended or adjusted under 35 U.S.C. 154(b) by 214 days.

(21) Appl. No.: 13/058,618

(22) PCT Filed: Aug. 11, 2009

(86) PCT No.: PCT/EP2009/060363
§ 371 (c)(1),
(2), (4) Date: Sep. 30, 2011

(87) PCT Pub. No.: WO2010/020561
PCT Pub. Date: Feb. 25, 2010

(65) Prior Publication Data
US 2012/0010435 A1 Jan. 12, 2012

(30) Foreign Application Priority Data
Aug. 16, 2008 (DE) .......................... 10 2008 038 021

(51) Int. Cl.
*C07C 43/00* (2006.01)

(52) U.S. Cl.
USPC ........................... 568/680; 568/672; 568/678

(58) Field of Classification Search
None
See application file for complete search history.

(56) References Cited

U.S. PATENT DOCUMENTS

| | | | |
|---|---|---|---|
| 3,740,322 A * | 6/1973 | Wada et al. | 203/48 |
| 3,829,507 A | 8/1974 | Zey | |
| 3,962,347 A | 6/1976 | Herz | |
| 5,840,994 A | 11/1998 | Ninomiya et al. | |
| 7,553,994 B2 * | 6/2009 | Kuzuhara et al. | 568/680 |
| 2002/0033325 A1 | 3/2002 | Ninomiya et al. | |
| 2003/0139631 A1 * | 7/2003 | Muller et al. | 568/595 |

FOREIGN PATENT DOCUMENTS

| | | | |
|---|---|---|---|
| JP | 57011934 A | | 1/1982 |
| JP | 61021538 B | | 5/1986 |
| JP | 08157401 A | * | 6/1996 |
| JP | 2002047231 A | | 2/2002 |

OTHER PUBLICATIONS

International Search Report from co-pending Application PCT/EP2009/060363 dated Oct. 29, 2009, 4 pages.

* cited by examiner

*Primary Examiner* — Sudhakar Katakam
(74) *Attorney, Agent, or Firm* — Michael A. Miller

(57) ABSTRACT

The present invention relates to a method for isolating ditrimethylol propane from secondary trimethylol propane production streams.

10 Claims, No Drawings

METHOD FOR ISOLATING DI-TRIMETHYLOL PROPANE

The present invention relates to a process for isolating ditrimethylolpropane from secondary streams from trimethylolpropane production.

Ditrimethylolpropane (di-TMP) is a starting material for the preparation of alkyd resins, high-quality paints and coatings, plasticizers and lubricants.

It is known in principle that di-TMP is obtained as by-product in the production of trimethylolpropane (TMP) and can be isolated in the workup of TMP from secondary streams.

Trimethylolpropane is prepared industrially by reaction of formaldehyde and n-butyraldehyde in an aqueous medium in the presence of bases. Intermediates are monomethylolbutyraldehyde and dimethylolbutyraldehyde. The last step is the conversion of dimethylolbutyraldehyde into TMP, which is either effected by hydrogenation in the "hydrogenation process" or by means of a Cannizzaro reaction of dimethylolbutyraldehyde with formaldehyde and stoichiometric amounts of a base to form TMP and the corresponding formic acid salt.

The hydrogenation process requires complicated technologies such as catalytic hydrogenation under superatmospheric pressure, while the Cannizzaro processes are simple to carry out using, for example, sodium hydroxide, sodium carbonate or calcium hydroxide as base. A particular advantage is that calcium formate is formed as coproduct when calcium hydroxide is used as base and represents an additional material of value produced by the process.

In this context, processes by means of which the proportion of di-TMP in TMP can be increased by controlling specific conditions are also known. Thus, for example, JP 57011934 and JP 61021538 state that this can be achieved by means of a proportion of formaldehyde of less than 20%, based on the total amount of water and formaldehyde. JP 0815740 describes the preparation of TMP and di-TMP in a two-phase reaction system.

Furthermore, it is known from EP 0799 815 A that di-TMP can be prepared by reaction of 2-ethylacrolein with TMP and formaldehyde in the presence of a basic catalyst.

The work-up of crude TMP reaction solution from Cannizzaro processes is described in many variations. It generally comprises, after neutralization of the base remaining in the reaction mixture, steps for concentrating the aqueous crude solution, for example distilling off low boilers and water, followed by steps for separating off inorganic coproducts such as, in particular, formates and steps for purifying the reaction product TMP.

The inorganic formates are generally separated off, after concentration, by filtration of the precipitated formats or by means of an extraction step in which TMP and organic by-products are separated off from the aqueous formate solution. An extraction step for separating TMP and di-TMP from the inorganic formates has the disadvantage that an additional stream matched to the total amount of TMP product has to be circulated, vaporized and condensed, which is unfavorable in terms of energy consumption.

After formates have been separated off, the target product TMP is generally distilled one or more times to purify it further. In these distillations, the di-TMP typically remains in the bottoms from the TMP distillation. Owing to its high boiling point, di-TMP itself can be obtained by distillation without decomposition only with a high technical outlay.

DE 2058518 describes a method of separating di-TMP from the remaining bottoms by steam distillation under reduced pressure. This method has the disadvantage that large amounts of steam are required and gives only a very impure product which has to be purified further by a multiple crystallization from an organic solvent.

Di-TMP accumulates in the bottoms from the TMP distillation. These bottoms therefore typically serve as suitable starting point for di-TMP recovery.

It is therefore an object of the present invention to obtain di-TMP in high purity from secondary streams from TMP production.

This object is achieved according to the invention by a process for isolating di-TMP from distillation bottoms from a TMP distillation, which is characterized in that a) the distillation bottoms are taken up in a suitable solvent and admixed, with introduction of mixing energy, with water and optionally an acid in such an amount that a multiphase system, preferably a two-phase system, composed of at least one organic solvent phase and a viscous residue phase is formed, b) the viscous residue phase is separated from the organic solvent phase by phase separation, c) the organic solvent phase obtained as per step b) is extracted with water, d) organic solvent present in the aqueous phase obtained as per step c) is removed and e) di-TMP is isolated from the aqueous phase obtained as per step d).

Suitable distillation bottoms from a TMP distillation are, in particular, those which have been obtained by distillation of TMP-containing crude products having a TMP content of less than 98% by weight, preferably less than 95% by weight, where the TMP-containing crude products have been produced by a process comprising at least the following steps:

i) reaction of formaldehyde and n-butyraldehyde in an aqueous medium in the presence of an inorganic base, ii) at least partial removal of substances having boiling points higher than that of TMP, in particular water and formaldehyde, iii) at least partial removal of inorganic formates.

The abovementioned TMP-containing crude products are typically obtained in TMP production processes.

The TMP-containing crude products are optionally produced by a process which comprises the following step:

iv) neutralization of inorganic base after step i)

in addition to steps i), ii) and iii).

Step iii), viz, the at least partial removal of inorganic formates, can, for example, be carried out by extraction, filtration, sedimentation or centrifugation, preferably by filtration, sedimentation or centrifugation.

Preferred distillation bottoms of the abovementioned type are those in which the inorganic base in step i) is sodium hydroxide or calcium hydroxide, preferably calcium hydroxide.

The distillation bottoms used typically contain not only di-TMP but also amounts of trimethylolpropane and cyclic and linear formals of trimethylolpropane. The di-TMP content is typically in the range from 5% to 60% by weight, based on the mass of the distillation bottoms. The TMP content is typically in the range from 1% to 50% by weight, based on the mass of the distillation bottoms.

Furthermore, the distillation bottoms can additionally contain inorganic salts. These salts are typically formates.

The pH of the bottoms, measured as a 10% strength slurry in water, typically depends on the process by means of which the TMP-containing crude products have been obtained.

Typical values can be in the range from pH 6 to pH 10 under standard conditions.

In step a), the distillation bottoms are taken up in a suitable solvent.

In a preferred embodiment, the distillation bottoms are taken up in a suitable solvent at a temperature of from 50 to 100° C., preferably from 70 to 95° C., preferably from 75° C. to 85° C.

Suitable solvents for the extraction are solvents or mixtures of solvents which are incompletely miscible with water and have a boiling point between the softening point of the distillation bottoms and the temperature at which significant decomposition of the bottoms commences. Preference is given to solvents having boiling points in the range from 40 to 200° C., particularly preferably from 70 to 160° C., particularly preferably from 80° C. to 150° C. Examples of suitable solvents are aromatic and aliphatic hydrocarbons, esters, ethers, alcohols or ketones. Preference is given to ethers, esters or ketones. Particular preference is given to cyclohexanone, methyl isobutyl ketone, ethyl acetate and butyl acetate or mixtures of such solvents.

The appropriate amount of solvent depends on the viscosity and the softening point of the distillation bottoms and can easily be determined by a person skilled in the art by means of a preliminary experiment on particular distillation bottoms. Preference is given to amounts of solvent which range from the amount of bottoms up to ten times this amount. Preference is given to amounts of from 1 to 8 times the amount of distillation bottoms, particularly preferably amounts ranging from twice to five times the amount of bottoms.

Furthermore, the bottoms are admixed with water and optionally, but preferably, an acid in such an amount that a multiphase system composed of at least one organic solvent phase and a viscous residue phase is formed.

Suitable amounts of water and acid depend on the composition and the pH of the bottoms and can easily be determined by a person skilled in the art by means of a preliminary experiment on particular distillation bottoms. Here, water is firstly added in an amount of from about 5 to 10% by weight, based on the distillation bottoms, while stirring gently and acid is then added a little at a time until any fine solid present has dissolved and a second phase settles out.

Preference is given to adding only such an amount of water that no separate, aqueous phase is formed. The amount of water to be added is typically in the range from 1 to 100% by weight, based on the mass of the distillation bottoms used, preferably from 5 to 30% by weight.

The amount of acid optionally used is typically in the range from 0.5 to 10% by weight, based on the distillation bottoms used, preferably in the range from 0.5 to 5% by weight. The amount of acid to be used is typically higher the more strongly alkaline the distillation bottoms used are.

Suitable acids are in principle all acids, with preference being given to organic acids and those inorganic acids which do not form sparingly soluble salts with any cations present in the distillation bottoms. For the purposes of the invention, sparingly soluble salts are those which have a maximum solubility of less than 5 g/l in water at 20° C. Particular preference is given to organic acids, very particularly preferably formic acid and acetic acid.

The acid and the water can also be introduced together or as dilute aqueous solutions of the acids.

In a preferred embodiment, the introduction of mixing energy, which can be effected by means of, for example, mixing devices known per se, e.g. stirrers, is switched off and the mixture is subsequently allowed to settle for from 5 minutes to 24 hours, preferably from 5 minutes to 8 hours, particularly preferably from 10 minutes to 4 hours.

In a likewise preferred embodiment, from about 0.05 to 5% by weight, preferably from 0.1 to 1.0% by weight, of activated carbon, based on the distillation bottoms, is additionally added to the multiphase system.

In step b), the viscous residue phase is separated from the organic solvent phase by phase separation in a manner known per se, e.g. by precipitation.

In a further embodiment of the invention, the viscous residue phase is again admixed with from 50 to 200% by weight of organic solvent, preferably heated and again allowed to settle. In this way, an oil which is significantly more fluid than the original viscous residue phase is obtained as lower phase. The supernatant organic phase obtained in this way is preferably reused for the same purpose in the next batch.

In step c), the organic solvent phase obtained as per step b) is extracted with water. The extraction is preferably carried out after filtration of the organic solvent phase.

The amount of water used for the extraction is, for example, from 2 to 100% by weight, preferably up to 40% by weight, but is at least high that a separate aqueous phase can form.

The aqueous phase is separated off and the organic phase is optionally but preferably extracted at least once more with water.

In a preferred variant, the organic phase after the water extraction is reused in step a).

In step d), organic solvent which is present in the aqueous phase obtained as per step c) or the optionally combined aqueous phases is removed.

The removal can be carried out in a manner known per se, for example and preferably by distillation.

The distillation can, for example, occur at a pressure in the range from 950 to 10 mbar. The distillation is preferably continued until the organic solvent from the bottoms has been removed to an extent of at least 90%, preferably at least 98%, from the aqueous phase.

In step e), di-TMP is isolated from the aqueous phase, preferably by crystallization.

In a preferred embodiment, the distillation residue from step d) is diluted with water so that the di-TMP content is in the range from 10 to 25% by weight, preferably from 10 to 20% by weight.

The mixture is then preferably heated until a clear solution is present and then cooled slowly while stirring at a cooling rate in the range from 0.5° C. to 6° C. per hour until crystallization commences.

To complete crystallization, the mixture is maintained at a temperature of preferably below 10° C. for from 0.5 hour to 8 hours. The precipitated crystals are, for example, separated off by filtration, centrifugation or a similar process, optionally washed and dried.

In a preferred variant, the crystallization mixture is seeded at a suitable temperature, for example in the range from 25 to 15° C. Seed crystals can, for example, be taken from a previous batch and triturated in water or by sudden cooling of a small portion of the crystallization mixture.

In another preferred variant, a suspension of di-TMP in water at a temperature of close to 0° C. is placed in a vessel and the warm crystallization solution is introduced over a period of from 0.25 to 24 hours, preferably from 0.5 to 12 hours, at such a rate that the initially charged mixture remains at the temperature originally set. After the addition is complete, the mixture is stirred for from 0.5 hour to 8 hours to complete the crystallization.

In another preferred process variant, the moist, washed product is melted, residual solvent is removed by distillation and the melt is, for example, shaped on a flake roller or a pastille-producing apparatus.

In a preferred variant, the process of the invention or individual steps thereof is/are carried out semicontinuously or continuously.

EXAMPLES

General

Content determinations were carried out by means of GC using an internal standard; calcium contents were determined titrimetrically using Titriplex solution Example 1 (for Comparison)

Extraction of the Bottoms with Water as Described in DE2358297

200 g of distillation bottoms containing 6.5% by weight of trimethylolpropane, 34% by weight of di-TMP, 24.3% by weight of linear TMP formal and 2.5% by weight of calcium and having a pH of 9 as 10% strength aqueous suspension in water at 20° C. were admixed with 400 g of water at 40° C. while stirring. A suspension of a dark sticky mass in water was obtained and could not be filtered. Even after addition of a further 400 ml of water and heating to 80° C., the tarry mass remained undissolved in the water.

Example 2 (for Comparison)

Extraction of the Bottoms with Organic Solvents as Described in EP1491521

200 g of distillation bottoms containing 6.5% by weight of trimethylolpropane, 34% by weight of di-TMP, 24.3% by weight of linear TMP formal and 2.5% by weight of calcium and having a pH of 9 as 10% strength aqueous suspension in water at 20° C. were admixed with 800 g of ethyl acetate at 80° C. while stirring. This gave a light-colored suspension which even after heating for a number of hours did not form a clear solution. The light-colored suspension could be filtered only with difficulty.

Example 3

Extraction According to the Invention of Distillation Bottoms 200 g of distillation bottoms containing 6.5% by weight of trimethylolpropane, 34% by weight of di-TMP, 24.3% by weight of linear TMP formal and 2.5% by weight of calcium and having a pH of 9 as 10% strength aqueous suspension in water at 20° C. were admixed with 800 g of butyl acetate at a bath temperature of from 80 to 90° C. while stirring. At 70-80° C., 20 g of water were added and the mixture was briefly allowed to settle. At 80° C., 6 g of formic acid (99.5% strength by weight) and 1 g of activated carbon were added while stirring carefully. After brief stirring, the stirrer was switched off and the mixture was maintained at 80° C. for half an hour. During this time, a dark, viscous phase settled out. The supernatant organic solution was decanted off and filtered through a fluted filter.

The viscous phase from the first extraction of the bottoms was once again admixed with the same mass of butyl acetate and heated to 125° C. The mixture was allowed to settle again and a fluid oil was obtained as lower phase.

The still hot organic phase from the first extraction was admixed with 60 g of water and cooled to 25° C. The phases were separated and the organic phase was once again extracted with 20 g of water at 25° C.

The aqueous phases were combined and distilled at a temperature at the top of 95° C. Here, 92 g of a two-phase mixture of butyl acetate and water were distilled off on a rotary evaporator at a pressure of 100 mbar. This left 180 g of liquid residue which was made up to 480 g with water for the crystallization and contained 67.8 g of di-TMP (14.1% by weight).

Example 4

Batch Crystallization 147 g of a solution produced in a manner analogous to Example 3 and containing 13.9% by weight of di-TMP were seeded at 22° C. with a suspension of di-TMP in water, cooled to −2° C. over a period of 24 h, stirred for another three hours at −2° C. and filtered. The filter cake was washed twice with 50 ml of ice water, sucked dry and the crystals were dried at up to 60° C. in a vacuum drying oven. This gave 16.2 g of di-TMP having a purity of 98.3%, corresponding to 78% of the feed to the crystallization.

Example 5

Batch Crystallization

The procedure as described in Example 4 was repeated, except that cooling was carried out over 8 hours. This gave 16.4 g of dried di-TMP having a purity of 98.9%, corresponding to 80% of the feed to the crystallization.

Example 6

Extraction of the Distillation Bottoms with Recirculation of the Butyl Acetate Phase The procedure as described in Example 4 was repeated except that the azeotropically dewatered butyl acetate phase from Example 3, which additionally contained 11.8 g of di-TMP, was reused in place of fresh butyl acetate. This gave 480 g of an aqueous solution containing 78.3 g of di-TMP.

Example 7

Semibatch Crystallization with Recirculation of the Washing Water 200 ml of washing water from an earlier crystallization, which contained 9.9 g of di-TMP, were brought to 10° C. and seeded with a suspension of di-TMP in water. The warm aqueous solution from Example 6 was added dropwise over a period of three hours. The temperature of the initial charge was maintained at 10° C. during the dropwise addition. The mixture was stirred at 5° C. for 2 hours, the solid was filtered off by suction filtration, the filter cake was washed twice with 100 ml each time of ice water, sucked dry and dried at 60° C. in a vacuum drying oven. This gave 54.0 g of di-TMP having a purity of 99.4%, corresponding to 77% of the content of the distillation residue used.

What is claimed is:

1. A process for isolating di-TMP from distillation bottoms from a TMP distillation, characterized in that
   a) taking up the distillation bottoms in a solvent and admixing by the introduction of mixing energy with water and optionally an acid in such an amount that a multiphase system is formed composed of at least one organic solvent phase and a viscous residue phase,
   b) separating the viscous residue phase from the organic solvent phase by phase separation,
   c) extracting the organic solvent phase obtained as per step b) with water,
   d) removing the organic solvent present in the aqueous phase obtained as per step c); and
   e) isolating di-TMP from the aqueous phase obtained as per step d).

2. The process as claimed in claim 1, characterized in that acid is additionally added in step a).

3. The process as claimed in claim 1, characterized in that a two-phase system is formed in step a).

4. The process as claimed in claim 1, characterized in that distillation bottoms which have been obtained by distillation of TMP-containing crude products having a TMP content of less than 98% by weight are used as distillation bottoms from a TMP distillation, where the TMP-containing crude products have been produced by a process comprising at least the following steps:
   i) reacting formaldehyde and n-butyraldehyde in an aqueous medium in the presence of an inorganic base,
   ii) removing, at least partially, substances having boiling points higher than that of TMP, and
   iii) removing, at least partially, inorganic formates.

5. The process as claimed in claim 4, characterized in that sodium hydroxide or calcium hydroxide is used as inorganic base in step i).

6. The process as claimed in claim 1, characterized in that the distillation bottoms used have a di-TMP content in the range of 5% to 60% by weight, based on the mass of the distillation bottoms.

7. The process as claimed in claim 1, characterized in that solvents comprise those solvents which are incompletely miscible with water and have a boiling point in the range from 40 to 200° C.

8. The process as claimed in claim 1, characterized in that from 0.05 to 5% by weight of activated carbon, based on the distillation bottoms, is additionally added to the multiphase system in step a).

9. The process as claimed in claim 1, characterized in that di-TMP is isolated from the aqueous phase by crystallization in step e).

10. The process as claimed in claim 1, characterized in that the process or individual steps from among steps a) to e) is/are carried out semicontinuously or continuously.

* * * * *